US006737411B2

(12) United States Patent
Valeriano et al.

(10) Patent No.: US 6,737,411 B2
(45) Date of Patent: May 18, 2004

(54) RACEMIZATION AND ENANTIOMER SEPARATION OF CLOPIDOGREL

(75) Inventors: Merli Valeriano, Lecco (IT); Paola Daverio, Milan (IT); Stefano Bianchi, Como (IT)

(73) Assignee: Teva Pharmaceutical Industries Ltd., Petah Tiqva (IL)

(*) Notice: Subject to any disclaimer, the term of this patent is extended or adjusted under 35 U.S.C. 154(b) by 0 days.

(21) Appl. No.: 10/302,357

(22) Filed: Nov. 22, 2002

(65) Prior Publication Data

US 2004/0024011 A1 Feb. 5, 2004

Related U.S. Application Data

(60) Provisional application No. 60/400,738, filed on Aug. 2, 2002.

(51) Int. Cl.⁷ .................. A61K 31/47; C07D 515/02
(52) U.S. Cl. ........................ 514/39; 546/114
(58) Field of Search ............... 514/301; 546/114

(56) References Cited

U.S. PATENT DOCUMENTS

| 4,529,596 | A | 7/1985 | Aubert et al. |
| 4,847,265 | A | 7/1989 | Badorc et al. |
| 5,036,156 | A | 7/1991 | Bouisset et al. |
| 5,132,435 | A | 7/1992 | Bousquet et al. |
| 5,204,469 | A | 4/1993 | Descamps et al. |
| 5,576,328 | A | 11/1996 | Herbert et al. |
| 6,080,875 | A | 6/2000 | Castro et al. |
| 6,180,793 | B1 | 1/2001 | Bakonyi et al. |
| 6,215,005 | B1 | 4/2001 | Heymes et al. |
| 6,258,961 | B1 * | 7/2001 | Bakonyi et al. ........ 549/77 |
| 6,429,210 | B1 | 8/2002 | Bousquet et al. |
| 6,504,030 | B1 | 1/2003 | Bousquet et al. |
| 2002/0177712 | A1 | 11/2002 | Pandey et al. |
| 2002/0198229 | A1 | 12/2002 | Bousquet et al. |

FOREIGN PATENT DOCUMENTS

| EP | 0 281 459 | 9/1988 |
| FR | 2 769 313 | 4/1999 |
| WO | WO 98/04259 | 2/1998 |
| WO | WO 98/39286 | 9/1998 |
| WO | WO 98/39322 | 9/1998 |
| WO | WO 98/51681 | * 11/1998 |
| WO | WO 98/51682 | 11/1998 |
| WO | WO 98/51689 | 11/1998 |
| WO | WO 99/18110 | 4/1999 |
| WO | WO 99/65915 | 12/1999 |
| WO | WO 00/27840 | 5/2000 |
| WO | WO 00/66130 | 11/2000 |
| WO | WO 02/059128 | 8/2002 |

OTHER PUBLICATIONS

Reist et al., "Very Slow Chiral Inversion of Clopidogrel in Rats: A Pharmacokinetic and Mechanistic Investigation," Drug Metabolism and Disposition, vol. 28, No. 12, Sep. 11, 2000, pp. 1405–1410.

* cited by examiner

Primary Examiner—D. Margaret Seaman
(74) Attorney, Agent, or Firm—Kenyon & Kenyon (57) ABSTRACT

Processes for separation of enantiomers of clopidogrel, and converting one enantiomer of clopidogrel to another enantiomer of clopidogrel are provided. The enantiomers are separated by crystallizing the (S) enantiomer as camphor sulfonate salt from a hydrocarbon, or a mixture of a hydrocarbon and a co-solvent, preferably DMF:toluene. The (R) enantiomer is then racemized and recycled by reaction with a catalytic amount of a base, preferably with t-butoxide.

64 Claims, 2 Drawing Sheets

Illustration of Example 3:

Illustration of Example 4:

FIG. 1

Illustration of Example 5:

Illustration of Example 6:

FIG. 1
(Continued)

RACEMIZATION AND ENANTIOMER SEPARATION OF CLOPIDOGREL

CROSS-REFERENCE TO RELATED APPLICATIONS

This application claims the benefit of provisional application Ser. No. 60/400,738, filed Aug. 2, 2002 which is incorporated herein by reference.

FIELD OF THE INVENTION

The present invention relates to the stereochemistry of clopidogrel.

BACKGROUND OF THE INVENTION

Atherosclerosis is the buildup of plaque in the wall of the arteries leading to a thickening and a reduction in elasticity of the arteries. Atherosclerosis results from injury to the inside layer of the artery. The injury is caused by common activities and diseases such as high cholesterol, high blood pressure, smoking and infection.

Plaques form on the inner walls of the artery at these sites of injury. The plaques are mainly composed of fatty tissue and smooth muscle cells. The formation of plaque often leads to blood clotting due to platelet aggregation at the site of the injury. This clotting may result in a reduction or elimination of blood flow to vital organs, causing heart attacks or other serious conditions. The plaque may also rupture and send a blood clot through the artery, referred to as an embolus, which if deposited in a smaller blood vessel may completely block blood flow.

Antiplatelet activity is desirable in fighting the often fatal results of atherosclerosis. Clopidogrel is an inhibitor of induced platelet aggregation which acts by inhibiting the binding of adenosine diphosphate to its receptor. Clopidogrel is metabolized by the liver into active form. Its antiplatelet activity is extended in that it stops any platelet activity even up to ten days after administration.

The chemical name of clopidogrel is methyl (+)-(S)-α-(o-chlorophenyl)-6,7-dihydrothieno[3,2-c]pyridine-5(4H)-acetate. It has the following structure:

Clopidogrel is disclosed in U.S. Pat. No. 4,529,596 (EP 99802, JP 59027895), U.S. Pat. Nos. 6,258,961, 5,036,156 (EP 420706, JP 3120286), U.S. Pat. No. 6,080,875 (EP 971915, JP 2001513806), U.S. Pat. No. 6,180,793 (EP 981529, JP 2001525829), FR 2769313, all of which are incorporated herein by reference for their disclosure and preparation of clopidogrel. U.S. Pat. No. 4,529,596 discloses a racemic mixture of clopidogrel and processes for preparing such mixture. U.S. Pat. No. 5,036,156 discloses a method for preparing an intermediate in the synthesis of clopidogrel, 2-chloro-α-bromophenylacetic acid, and a process for condensing its methyl ester with tetrahydrothienopyridine. FR 2769313 discloses an intermediate in the synthesis of clopidogrel, (R)-2-benzenesulfonyloxy-2-(2-chlorophenyl) acetic acid methyl ester, and processes for its preparation. FR 2769313 further discloses converting the ester to clopidogrel by nucleophilic substitution with tetrahydrothienopyridine. U.S. Pat. No. 5,036,156 discloses preparation of pyridine drivatives by reacting a benzaldehyde with tribromomethane and potassium hydroxide in water and in the presence of an inert solvent.

Clopidogrel's platelet inhibiting activity makes it an effective drug for reducing the incidence of ischemic strokes, heart attacks or claudication due to vascular diseases such as atherosclerosis. By inhibiting platelet aggregation, clopidogrel reduces the chance of arterial blockage, thus preventing strokes and heart attacks. U.S. Pat. No. 5,576,328 describes a method of preventing the occurrence of a secondary ischemic event by administration of clopidogrel, and is incorporated herein by reference.

Recent studies have shown that clopidogrel is more effective in blocking platelet aggregation than aspirin and is much gentler on the gastrointestinal tract. Clopidogrel is more effective than aspirin even at much lower dosage. A dosage of 75 mg of base equivalent has been shown to be more effective than a dosage of 325 mg of aspirin. In addition to being more effective, clopidogrel produces much less gastrointestinal bleeding than aspirin.

Clopidogrel is administered as its bisulfate (syn. hydrogensulfate) salt. Clopidogrel bisulfate has an empirical formula of $C_{16}H_{16}Cl\ NO_2S.H_2SO_4$. It is currently being marketed as PLAVIX® tablets, which contain about 98 mg clopidogrel bisulfate, which is the equivalent of 75 mg clopidogrel base. PLAVIX® is a white to off-white powder that is practically insoluble in water at neutral pH but highly soluble at acidic pH. It dissolves freely in methanol, somewhat in methylene chloride, and poorly in ethyl ether.

The enantiomer (S) clopidogrel is particularly preferred since it is the pharmaceutically active compound.

U.S. Pat. No. 6,080,875 (EP 971915, JP 2001513806), incorporated herein by reference, prepares (S) clopidogrel by reaction of sodium 2-thienylglycidate with (S) 2-chloro phenyl glycine in the presence of cyanoborohydride.

U.S. Pat. No. 6,180,793 (EP 981,529, JP 2001525819) and related publications WO 98/51681, WO 98/51682 and WO/51689, incorporated herein by reference, prepare the (S) enantiomer by methods that control the chirality of the intermediates used in the synthesis of clopiodogrel to reduce formation of the (R) enantiomer. U.S. Pat. No. 6,180,793 and the related art disclose processes for synthesizing (S) clopidogrel by reaction of an activated form of 2-thiophene ethanol with (S)-2-chlorophenyl glycineamide, (S)-2-chlorophenyl-α-amino acetonitrile or (S)2-chlorophenyl glycine methyl ester. After condensation, the resulting compound is cyclicized, hydrolyzed and esterified.

WO 98/39286, incorporated herein by reference, discloses a racemization process for phenyl glycine esters. A mixture of enantiomers of phenyl glycine ester is treated with a carbonyl compound in the presence of a carboxylic acid and a single enantiomer of an N-protected α-amino acid as resolving agent. The formation of an imino intermediate causes the racemization of the starting product and the precipitation of a single diastereomeric salt. After hydrolysis of the salt, an enantiomer of phenyl glycine ester is obtained.

U.S. Pat. No. 4,847,265 (EP 291459, JP 63203684) discloses methods for separating one enantiomer of clopidogrel from another by selective crystallization of the camphor sulfonate of the (S) enantiomer. The '265 patent discloses crystallizing the (S) enantiomer from dimethylformamide ("DMF"), ketones, and alcohols, though crystallization with acetone is primarily disclosed. U.S. Pat. No. 5,132,435 (EP 465358, JP 3055819), U.S. Pat. No. 6,215,005 and U.S. Pat. No. 6,258,961, incorporated herein by reference, also disclose separating the (S) enantiomer of clopidogrel by crystallization of the camphor sulfonate from acetone.

U.S. Pat. No. 5,204,469 (EP 466569, JP 4230387) discloses an enantioselective process for synthesis of clopidogrel through reaction of (+)-2-chloro phenylglycine and an activated form of 2-thiophene ethanol followed by cyclization with formaldehyde.

WO 00/27840 (EP 1129087) discloses using a base to racemize an amide intermediate used in the synthesis of clopidogrel. The process of WO 00/27840 requires going through an amide intermediate, which is not always used in preparing clopidogrel, as illustrated by Examples 1 and 2 of the present invention. It is advantageous to prepare clopidogrel, and then racemize clopidogrel rather than the intermediate, and to skip the necessary conversion of the amide intermediate to an ester as required in WO 00/27840. WO 02/059128 also generally discloses racemization of an intermediate of clopidogrel and clopidogrel with an equimolar amount of a base, though an actual example is not provided regarding racemization of clopidogrel.

A problem with the preparation of clopidogrel is the presence of a therapeutically inactive enantiomer, the (R) enantiomer. The presence of the (R) enantiomer results in contamination of the main product, and reduces the yield by being a waste product. There is a need in the art to prepare the (S) enantiomer of clopidogrel substantially free of the (R) enantiomer in a facile manner suitable on an industrial scale.

SUMMARY OF THE INVENTION

In one aspect, the present invention provides a process for preparing (S) clopidogrel free base or a pharmaceutically acceptable salt thereof comprising the steps of reacting a mixture of (R) and (S) clopidogrel free base with levorotatory camphor sulfonic acid in a mixture of a $C_5$ to a $C_{12}$ hydrocarbon and a suitable co-solvent to precipitate (S) clopidogrel camphor sulfonate and converting (S) clopidogrel camphor sulfonate to clopidogrel free base or a pharmaceutically acceptable salt thereof. A preferred salt is the bisulfate salt. Preferably, the mixture contains from about 3% to about 20% (vou vol) of the co-solvent, more preferably about 5% to about 10% of the co-solvent. Preferably, the co-solvent is selected from the group consisting of DMF, butanol and acetone. Preferably, the hydrocarbon is an aromatic hydrocarbon, more preferably xylene, benzene, toluene and chlorobenzene, and most preferably toluene.

In another aspect, the present invention provides a process for racemizing (R) clopidogrel comprising reacting (R) clopidogrel with a catalytic amount of a base in a solvent to convert a portion of the (R) clopidogrel to (S) clopidogrel. Preferred bases are sodium t-butoxide, potassium t-butoxide, diisopropylamide, sodium hydride, potassium hydride, sodium methoxide and potassium methoxide. Preferably, the solvent is a hydrocarbon as described above. Preferably, the racemizing is carried out at a temperature of less than about 20° C., more preferably at a temperature of about 0° C.

In another aspect, the present invention provides a process for preparing a pharmaceutically acceptable salt of (S) clopidogrel comprising the steps of reacting a first mixture of (R) and (S) clopidogrel with levorotatory camphor sulfonic acid in a mixture of a $C_5$ to a $C_{12}$ hydrocarbon and a suitable co-solvent to precipitate a first (S) clopidogrel camphor sulfonate, racemizing (R) clopidogrel remaining in the mixture of the hydrocarbon and the co-solvent by reaction with a catalytic amount of a base to obtain a second mixture of (R) and (S) clopidogrel, precipitating both forms of clopidogrel from the second mixture of (R) and (S) clopidogrel by adding an acid to form a salt, converting the salt to a free base, repeating the first step of the process to obtain a second (S) clopidogrel camphor sulfonate from the free base and converting the first and second (S) clopidogrel camphor sulfonate to a pharmaceutically acceptable salt of (S) clopidogrel.

In another aspect, the present invention provides a process for preparing a pharmaceutically acceptable salt of (S) clopidogrel comprising the steps of reacting a first mixture of (R) and (S) clopidogrel with levorotatory camphor sulfonic acid in a mixture of a $C_5$ to a $C_{12}$ hydrocarbon and a suitable co-solvent to precipitate a first (S) clopidogrel camphor sulfonate, racemizing the (R) clopidogrel remaining in the mixture of the hydrocarbon and the co-solvent by reaction with a catalytic amount of a base to obtain a second mixture of (R) and (S) clopidogrel, reacting the second mixture of (R) and (S) clopidogrel with levorotatory camphor sulfonic acid to precipitate a second (S) clopidogrel camphor sulfonate and converting the first and the second (S) clopidogrel camphor sulfonate to a pharmaceutically acceptable salt of (S) clopidogrel.

In another aspect, the present invention provides a process for preparing (S) enantiomer of clopidogrel bisulfate comprising the steps of reacting a solution of (R) and (S) clopidogrel in toluene with a solution of levorotatory camphor sulfonic acid in DMF, thereby forming a first clopidogrel (S) camphor sulfonate as a precipitate, removing the DMF and excess camphor sulfonic acid, racemizing the (R) clopidogrel by reaction with a catalytic amount of a base in the toluene to form a mixture of clopidogrel (R) and (S), reacting the mixture of (R) and (S) clopidogrel with levorotatory camphor sulfonic acid in the toluene, thereby forming a second (S) clopidogrel camphor sulfonate as a precipitate and converting the first and the second (S) clopidogrel camphor sulfonate to (S) clopidogrel bisulfate.

In another aspect, the present invention provides a process for preparing (S) clopidogrel bisulfate comprising the steps of reacting a solution of clopidogrel (R) and (S) in toluene with a solution of levorotatory camphor sulfonic acid in DMF, thereby forming a first clopidogrel (S) camphor sulfonate as a precipitate, removing the DMF and excess camphor sulfonic acid, racemizing the (R) clopidogrel remaining in the toluene by reaction with a catalytic amount of a base in the toluene to form a mixture of (R) and (S) clopidogrel, adding sulfuric acid to the mixture of (R) and (S) clopidogrel to precipitate clopidogrel (R) and (S) as a bisulfate, converting the bisulfate to a free base, repeating the first step of the process to obtain a second (S) clopidogrel camphor sulfonate from the free base and converting the first and the second (S) clopidogrel camphor sulfonate to (S) clopidogrel bisulfate.

In another aspect, the present invention provides a process for preparing (S) clopidogrel bisulfate comprising the steps of reacting a solution of (R) and (S) clopidogrel in toluene with a solution of levorotatory camphor sulfonic in DMF, thereby forming (S) clopidogrel camphor sulfonate as a precipitate and converting (S) clopidogrel camphor sulfonate to clopidogrel bisulfate.

In another aspect the present invention provides a process for preparing (S) clopidogrel free base or a pharmaceutically acceptable salt thereof comprising the steps of reacting a mixture of (R) and (S) clopidogrel free base with levorotatory camphor sulfonic acid in a $C_5$ to a $C_{12}$ hydrocarbon to precipitate (S) clopidogrel camphor sulfonate and converting (S) clopidogrel camphor sulfonate to clopidogrel free base or a pharmaceutically acceptable salt thereof.

In another aspect, the present invention provides a process for preparing a pharmaceutically acceptable salt of (S) clopidogrel comprising the steps of reacting a mixture of (R) and (S) clopidogrel with levorotatory camphor sulfonic acid in a $C_5$ to a $C_{12}$ aromatic hydrocarbon to precipitate (S) clopidogrel camphor sulfonate, racemizing the (R) clopidogrel remaining in the hydrocarbon by reaction with a catalytic amount of a base in the hydrocarbon to obtain a mixture of (R) and (S) clopidogrel, recovering the (S) clopidogrel and converting the (S) clopidogrel to a pharmaceutically acceptable salt.

DETAILED DESCRIPTION OF THE INVENTION

Figure 1:
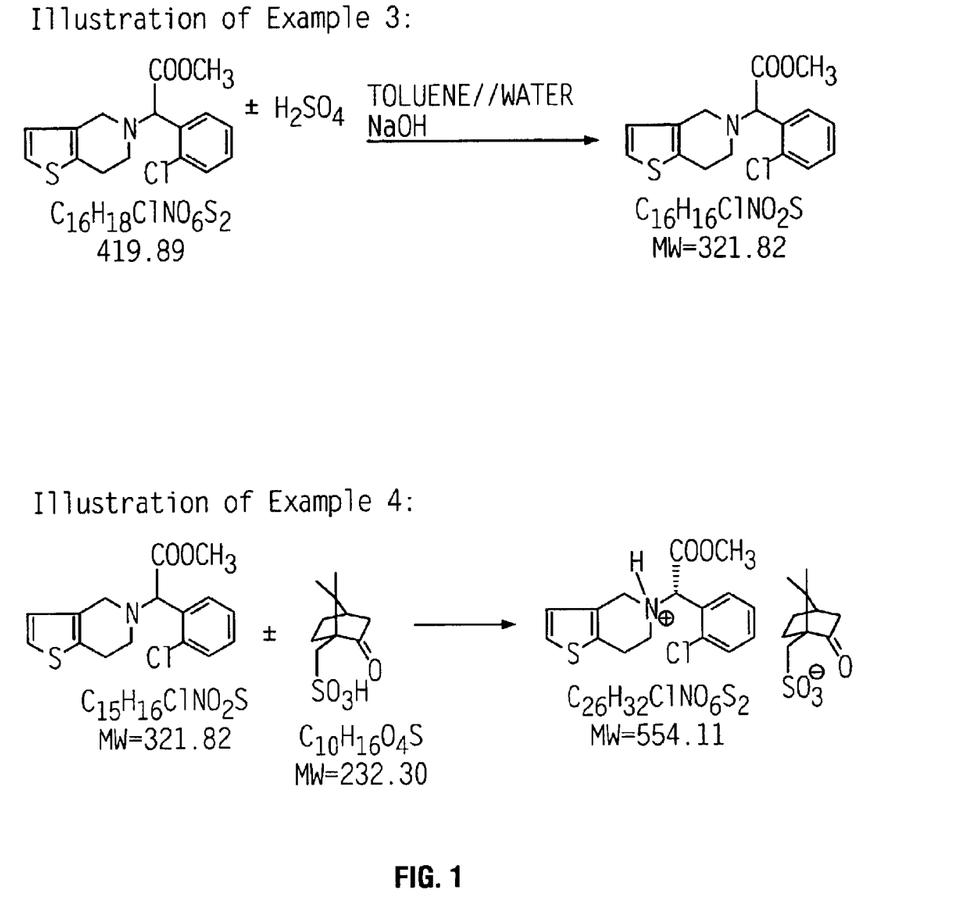
FIG. 1 provides a pictorial illustration of the various examples.

The present invention provides facile processes for separation of the (S) enantiomer of clopidogrel from a racemic mixture of the enantiomers, and recycling the (R) enantiomer after the separation step to produce more of the (S) enantiomer. The clopidogrel used in the present invention can be synthesized according to the disclosed methods of the present invention or any method known in the art.

The present invention uses bases for freeing the base of clopidogrel or deprotonating clopidogrel for racemization. One of skill in the art would appreciate that many bases can be used to free the base or deprotonate clopidogel. Examples of bases include, for example, an organic amine, an alkoxide, an alkali metal hydroxide, an alkaline earth metal hydroxide, an alkali metal hydride, an alkaline earth metal hydride or an alkali or alkaline earth metal carbonate or hydrogencarbonate salt. Specific examples of bases include, for example, 1,8-bis(N,N-dimethylamino)napthalene, sodium methoxide, sodium ethoxide, sodium phenoxide, sodium hydroxide, potassium hydroxide, calcium hydroxide, magnesium hydroxide, sodium hydride, potassium hydride, calcium hydride, sodium carbonate, potassium carbonate, sodium hydrogencarbonate, potassium hydrogencarbonate, calcium carbonate and basic alumina. The preferred base and its concentration can vary depending on the desired task. For example, when deprotonating, a strong base such as an alkoxide is preferred over a weak base such as an amine. Preferred bases for racemization by deprotonation are lithium diisopropylamide ("LDA"), potassium hydride, sodium hydride, sodium methoxide and t-butoxide.

To separate the (S) enantiomer of clopidogrel bisulfate from the racemic mixture, a racemic mixture of clopidogrel free base is first prepared by reacting the bisulfate salt with a base. Preferred bases are non-organic bases, particularly sodium/potassium carbonate or hydroxide.

Any formed sulfate, particularly sodium sulfate, can be removed by conventional techniques such as filtration. The free base is then crystallized from a mixture of a $C_5$ to a $C_{12}$ hydrocarbon and a suitable co-solvent in the presence of levorotatory camphor sulfonic acid.

In a preferred embodiment, a mixture of clopidogrel bisulfate is treated with a slight excess of sodium hydroxide in a $C_5$ to a $C_{12}$ hydrocarbon. The mixture used can have a higher proportion of one of the enantiomers in respect to the other, or be a racemic mixture. The resulting solution of clopidogrel free base in the hydrocarbon is then added to a solution of levorotatory camphor sulfonic acid in a suitable co-solvent of the hydrocarbon used. Suitable co-solvents are those that are miscible in the $C_5$ to a $C_{12}$ hydrocarbon used and allow for crystallization of (S) clopidogrel camphor sulfonate. Preferably, the co-solvent can be separated from the hydrocarbon by washing with water. Examples of such suitable solvents include $C_1$ to $C_4$ alcohols such as methanol, ethanol, iso-propanol and butanol, lower ketones such as acetone and lower amides such as dimethylformamide ("DMF"). Butanol for example, despite its relatively low miscibility with water, can be washed continuously and removed. The use of DMF as a co-solvent is preferred, particularly in a mixture with toluene. Preferred $C_5$ to $C_{12}$ hydrocarbons are substituted and unsubstituted aromatic hydrocarbons, such as benzene, xylene, toluene and chlorobenzene. A preferred aromatic hydrocarbon is toluene. In various embodiments, the combination of toluene with acetone, DMF and butanol may be used, with the combination of DMF/toluene being illustrated in the present invention.

The resulting mixture of the hydrocarbon and the co-solvent is at most 50%, more preferably from a 3% to about a 20%, most preferably from about a 5% to about a 10% co-solvent:hydrocarbon (vol/vol) mixture. The amount of co-solvent, such as DMF, influences the resolution rate and the diastereomic excess obtained. An excess amount of DMF slows down the crystallization process and lowers the yield.

The (S) enantiomer of clopidogrel is then crystallized out of the solution, leaving substantially the (R) enantiomer in the solution. The ratio of clopidogrel free base to camphor sulfonic acid is preferably from about a 1/0.6 to 1/0.8, more preferably about a 1/0.6 (mole/mole) of clopidogrel:camphor sulfonic acid. The ratio is in relation to both enantiomers of clopidogrel. The crystals are substantially in the form of (S) clopidogrel camphor sulfonate. Without being bound by any theory, it is believed that the (R) enantiomer, being unable to form a salt with levorotatory camphor sulfonic acid, remains in the solution. While, (S) clopidogrel camphor sulfonate, having low solubility for the solvent, crystallizes out of the solution. To accelerate crystallization, the solution may be seeded or the temperature of the solution reduced. Preferably the temperature is reduced to about 5° C. to about 25° C., with about 15° C. being preferred. The present invention encompasses both embodiments where crystallization is induced, or when crystallization occurs spontaneously upon contact.

The solution can be monitored during the crystallization process to ensure crystallization of substantially all of the (S) enantiomer. In a preferred embodiment, the solution is monitored with a polarimeter. For optimal result, the crystallization process is stopped when the optical rotation of the solution (mother liquor) remains constant for at least about 1 hour.

In another embodiment, a co-solvent is not used. Rather a hydrocarbon as described above is used as a solvent free of a co-solvent for reaction of clopidogrel free base with levorotatory camphor sulfonic, followed by precipitation. Preferably, the hydrocarbon contains only traces of other solvents, most preferably the hydrocarbon is pure.

The (S) clopidogrel camphor sulfonate can then be converted to (S) clopidogrel bisulfate in a routine fashion. The free base is first liberated by treating the camphor sulfonate with a base, as described above, preferably with sodium/potassium bicarbonate. Preferably a weak or dilute base is used to avoid racemization. In a preferred method, the (S) clopidogrel camphor sulfonate is dissolved in a mixture of water and an ester such as ethyl acetate or a ketone. Sodium/potassium bicarbonate and/or sodium hydroxide is then added to basify the water, resulting in the free base of (S) clopidogrel. The free base is then extracted out of the water with a suitable organic solvent, such as dichloromethane or ethylacetate, followed by concentration of the organic phase. The residue is added to a suitable solvent, such as acetone, in the presence of sulfuric acid, resulting in the precipitation of clopidogrel bisulfate.

The present invention also provides for processes which allow for recycling the (R) enantiomer left in the mother liquor. The processes of the present invention accomplish this recycling process by racemization of the (R) enantiomer into a mixture of (S) and (R) enantiomers, and separating the two enantiomers as described above. As one of skill in the art would appreciate, the recycling step can be repeated many times to recycle as much of the (R) enantiomer as possible. A small portion of the (R) enantiomer may be purged each time to improve overall efficiency of the process.

The racemization step can be carried out in the same or different solvent as prior steps. The solvent used for racemization however should be one that avoids reactivity problems with strong bases. Such reactivity can occur for example when using a ketone. DMF however could be used in the racemization step, but the subsequent camphor sulfonate salt is soluble in DMF. The substitution of DMF with another solvent, after racemization, would be needed for optimal crystallization. A preferred solvent for racemization is a hydrocarbon as described above.

The (R) enantiomer is racemized by treatment with a base. As used herein, "recemizing (R) clopidogrel" refers to obtaining an optically inactive mixture, or stopping the racemization process at any point to obtain an unequal mixture of the forms. The (R) clopidogrel can be contacted/reacted with a base in the presence or absence of (S) clopidogrel, i.e., reacting (R) clopidogrel with a base covers both embodiments. For example, it is unlikely that 100% of (S) clopidogrel would precipitate as the camphor sulfonate, thus leaving some (S) clopidogrel in the solution during the racemization step.

The mother liquor containing the (R) enantiomer is preferably washed first to remove any remaining camphor sulfonic acid. A preferred method of removing camphor sulfonic acid is by making the mother liquor alkaline, such as by using an aqueous solution of sodium bicarbonate. The organic phase is then separated from the resulting aqueous phase. The washing removes the co-solvent, leaving only traces of the co-solvent remaining during racemization.

A base can be used to racemize the (R) clopidogrel. A preferred inorganic base is sodium/potassium hydroxide, while a preferred organic base is a $C_1$ to a $C_4$ alkoxide. A particularly preferred base is sodium/potassium t-butoxide, which is more effective than sodium/potassium methoxide.

Bases, particularly alkoxides such as t-butoxide are highly reactive towards moisture, and in order for the t-butoxide added to be effective, the organic phase preferably has a low water content. Preferably, the water content of the organic phase is less than or equal to about 0.1%, more preferably 0.05%, as determined by the Karl Fischer method. After achieving an acceptable water level, a catalytic amount of potassium t-butoxide is added to the organic phase. Preferably, the amount of potassium t-butoxide is from about 0.01 to about 0.15 moles relative to both forms of clopidogrel, more preferably about 0.05 moles. The molar ratio also generally applies to other bases. Preferably, the t-butoxide is added to the organic phase at a temperature of less than about 20° C., more preferably at a temperature less than about 10° C., even more preferably at a temperature of less than about 5° C. and most preferably at a temperature. of about 0° C.

After addition of the t-butoxide, some of the (R) enantiomer converts to the (S) enantiomer, resulting in a mixture of the forms. A small amount of time, less than about one hour, more likely less than about 30 minutes is often sufficient to allow for the conversion. The racemization results in an optically inactive mixture.

After obtaining a mixture of the forms, the recovery of the forms can be done by conventional techniques. First, the t-butoxide is neutralized, for example by adding an acid. An example of an acid is acetic acid, whose addition results in formation of t-butanol. The organic phase is then preferably washed with water to remove the alcohol, the formed salt and any residual acid.

The organic phase is then preferably concentrated. Conventional techniques, such as evaporation under reduced pressure, heating or increasing surface area (i.e. rotary evaporator) can be used to concentrate the organic phase. The result of the concentration is preferably a thick oil.

The racemic mixture can then be crystallized by adding the oil to an organic solvent in the presence of sulfuric acid or another acid. Examples of suitable solvents include lower alcohols, esters, ethers and ketones (such as acetone). The preferred solvent may vary depending on whether the camphor sulfonate or the bisulfate is crystallized out of the solution. In a preferred embodiment, the oil is added to a toluene/DMF mixture, followed by addition of sulfuric acid, resulting in crystallization of a racemic mixture of clopidogrel bisulfate. The (S) enantiomer can then be separated from the racemic mixture as described above, i.e., by conversion to clopidogrel free base, precipitation as (S) clopidogrel camphor sulfonate salt and conversion to the desirable acid addition salt.

In another embodiment, the oil is added to a solvent such as acetone or a toluene/DMF mixture in the presence of levorotatory camphor sulfonic acid, resulting in precipitation of (S) clopidogrel camphor sulfonate. The (S) clopidogrel camphor sulfonate is then converted to the bisulfate by conventional techniques.

The present invention allows for a continuous process for preparing (S) clopidogrel, wherein (S) clopidogrel is constantly removed, while additional (S) clopidogrel is added as a starting material or from recycling of the (R) enantiomer. The continuous recycling process allows for an efficient process on industrial scale. In a preferred embodiment, the racemic mixture generated by recycling the (R) enantiomer is crystallized out as a bisulfate salt or another salt, and used as a starting material by conversion to the free base. In another embodiment, the (S) clopidogrel is crystallized out of the recycled mixture as camphor sulfonate, and then converted to the bisulfate. A small portion of the waste material may be purged as the process proceeds.

The processes of the present invention can be used to prepare any pharmaceutically acceptable salt of clopidogrel. These processes have been illustrated so far with the bisulfate salt. Examples of other pharmaceutically acceptable salts are disclosed in U.S. Pat. No. 4,847,265, incorporated herein by reference: acetic, benzoic, fumaric, maleic, citric, tartaric, gentisic, methane-sulfonic, ethanesulfonic, benzenesulfonic and laurylsulfonic, taurocholate and hydrobromide salts. Of these, taurocholate and hydrobromide salts, like the bisulfate salt, exhibit better pharmaceutical properties. The processes for preparing these other salts is the same as that for the bisulfate salt except instead of sulfuric acid another acid is added to obtain the desired acid addition salt. These salts can be converted to the free base in a similar manner as that discussed for the bisulfate salt.

As a platelet inhibitor, clopidogrel is effective at suppressing the lethal effects of blood clotting. Platelet aggregation often occurs around damaged blood vessels. The blood vessels may only have minor fissures or plaques to induce platelet aggregation.

Platelet aggregation leads to the blockage of arteries, thus increasing the risk of primary and secondary strokes and heart attacks. By inhibiting platelet aggregation, clopidogrel bisulfate reduces the risk of heart attacks and strokes. Clopidogrel is particularly effective in the secondary prevention of ischemic events, which are defined in the art as a decrease in the blood supply to a bodily organ, tissue, or part caused by constriction or obstruction of the blood vessels.

Pharmaceutical compositions of the present invention contain the (S) enantiomer of clopidogrel bisulfate, optionally in a mixture with other active ingredients. In addition to the active ingredient(s), the pharmaceutical compositions of the present invention may contain one or more excipients. Excipients are added to the composition for a variety of purposes.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dixoide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, clopidogrel bisulfate and any other solid excipients are dissolved or suspended in a liquid carrier such as water, vegetable oil, alcohol, polyethylene glycol, propylene glycol or glycerin.

Liquid pharrnaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate.

Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

Capsules, tablets and lozenges, and other unit dosage forms preferably contain a base equivalent of about 75 mg, which is about 98 grams of clopidogrel bisulfate. The unit dosage form as used herein refers to the amount of the various forms of clopidogrel contained in the vehicle of administration, such as a tablet or a capsule. In a preferred embodiment, the unit dosage in a tablet for oral administration contains a base equivalent of about 25 mg to 150 mg. Most preferably, it is about 75 mg base equivalent. One skilled in the art would appreciate that other unit dosages may be made as necessary in a routine fashion.

Instrumentation Used:

The polarimiter used was Perkin Elmer® 241, and Karl Fischer analysis was done with Metrohm® 703.

The following examples further illustrate the present invention:

EXAMPLES

Example 1

Synthesis of Tetrahydrothienopyridine Hydrochloride 2-thienylethlamine was reacted with formaldehyde to give the corresponding formimine, which was then added to a solution of hydrochloric acid in DMF, resulting in cyclization to tetrahydrothienopyridine hydrochloride. The DMF used was anhydrous, $KF \leq 0.05\%$, to avoid formimine hydrolysis.

Example 2

Synthesis of Racemic Clopidogrel

Tetrahydrothienopyridine hydrochloride from Example 1 was reacted with α-bromo-2-chlorophenyl acetic acid methyl ester in acetone in the presence of potassium carbonate to give racemic clopidogrel. After inorganic salt filtration, the product was recovered as bisulfate, by addition of sulfuric acid.

Example 3

Preparation of Clopidogrel Free Base from Bisulfate

Clopidogrel bisulfate was suspended in a mixture of toluene and water. The pH of the suspension was adjusted to 11–12 with 50% sodium hydroxide solution. The reaction mixture was kept at 35° C., followed by phase separation. The organic phase was filtered through decolorizing clay. The filtrate was evaporated under vacuum until all of the toluene was removed. The resulting oil contained clopidogrel free base.

Example 4

Resolution by Camphorsulfonic Salt Formation

A reactor was charged with racemic clopidogrel of Example 3 and toluene. Another reactor was charged with DMF and (−)-(R)-camphorsulfonic acid (CSA/Rac clopidogrel=0.6/1 mole/mole) and heated to 30° C. The toluene solution was added to the DMF/(−)-(R)-camphorsulfonic acid solution. All reagents were measured on the basis of the calculated amount of racemic clopidogrel used.

The batch solution was maintained at 30° C. and seeded with (+) Clopidogrel camphor sulfonate, then cooled to 15° C. to affect crystallization of the product. The rotation of the filtrates from a filtered sample was measured. Samples were taken every 30 minutes until two of the results taken were within 0.01 of each other, within range of −0.455±0.035 or until the rotation began to decrease. The product was filtered, washed with toluene, then dried under vacuum at $\leq 35°$ C.

Example 5

Bis Resolution (Camphorsulfonic Salt Formation)

(+)-(S)-a-(2-Chlorophenyl)-4,5,6,7-tetrahydrothieno[3,2-C]Pyridyl-5-acetic acid methyl ester, (−) CSA salt was suspended in acetone at reflux for 1 hour, cooled to room temperature, filtered and dried under vacuum at a temperature of 35° C.

Example 6
Preparation of Clopidogrel Bisulfate Form 1 from the Camphor Sulfonate Salt (+) Clopidogrel (−) CSA salt was added to ethyl acetate and water. Next sodium hydroxide was charged to the batch followed by sodium bicarbonate. The organic phase was separated and washed with water, and then decolorized with charcoal. Once the charcoal was filtered, the batch was concentrated. The residue was dissolved in acetone, and then sulfuric acid was added followed by clopidogrel polymorph seed. The crystals were aged under stirring, then filtered and washed with acetone. The crystals were then dried under vacuum at a temperature of less than 25° C.

Example 7
Racemization and Racemic Bisulfate Recovery

The mother liquor from Example 4 was washed with 6% sodium bicarbonate solution. The two resulting phases were separated. After separation, the organic phase was dried by azeotropic distillation under reduced pressure until KF≦0.05%. A catalytic amount of potassium tert-butoxide was added at 0° C., and racemization occurred within 20 minutes. After neutralization of potassium tert-butoxide with acetic acid, and washing with water, the organic solution was concentrated until a thick oil was obtained. After dissolution in acetone, sulfuric acid was added and the racemic clopidogrel was recovered as bisulfate.

Example 8
Racemization and (S) Clopidogrel Camphor Sulfonate Recovery

The mother liquor from Example 4 is washed with 6% sodium bicarbonate solution. The two resulting phases are separated. After separation, the organic phase is dried by azeotropic distillation under reduced pressure until KF≦0.05%. A catalytic amount of potassium tert-butoxide is added at 0° C., and racemization occurs within 20 minutes. After neutralization of potassium tert-butoxide with acetic acid, and washing with water, the organic solution is concentrated until a thick oil is obtained. After dissolution in acetone, camphor sulfonic acid is added and (S) clopidogrel is recovered as camphor sulfonate. The (S) clopidogrel camphor sulfonate is then added to a base, followed by addition of an acid to obtain the desired acid addition salt.

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. All references mentioned herein are incorporated in their entirety.

What is claimed is:

1. A process for preparing (S) clopidogrel free base or a pharmaceutically acceptable salt thereof comprising the steps of:
   a) reacting a mixture of (R) and (S) clopidogrel free base with levorotatory camphor sulfonic acid in a mixture of a $C_5$ to a $C_{12}$ hydrocarbon and a suitable co-solvent to precipitate (S) clopidogrel camphor sulfonate; and
   b) converting (S) clopidogrel camphor sulfonate to clopidogrel free base or a pharmaceutically acceptable salt thereof.

2. The process of claim 1, wherein the salt is a bisulfate salt.

3. The process of claim 1, wherein the mixture contains from about 3% to about 20% (vol/vol) of the co-solvent.

4. The process of claim 3, wherein the mixture contains from about 5% to about 10% of the co-solvent.

5. The process of claim 1, wherein the co-solvent is selected from the group consisting of DMF, butanol and acetone.

6. The process of claim 1, wherein the hydrocarbon is an aromatic hydrocarbon.

7. The process of claim 6, wherein the aromatic hydrocarbon is selected from the group consisting of xylene, benzene, toluene and chlorobenzene.

8. The process of claim 7, where the hydrocarbon is toluene.

9. The process of claim 1, comprising a preliminary step of reacting a mixture of clopidogrel (R) and (S) bisulfate with a base.

10. A process for racemizing (R) clopidogrel comprising reacting (R) clopidogrel with a catalytic amount of a base in a solvent to convert a portion of the (R) clopidogrel to (S) clopidogrel.

11. The process of claim 10, wherein the catalytic amount is less than about 0.15 moles relative to clopidogrel.

12. The process of claim 10, further comprising a step of crystallizing a pharmaceutically acceptable salt or a camphor sulfonate salt of the (S) clopidogrel.

13. The process of claim 12, wherein the salt is a bisulfate salt.

14. The process of claim 10, wherein the base is selected from the group consisting of sodium t-butoxide, potassium t-butoxide, diisopropylamide, sodium hydride, potassium hydride, sodium methoxide and potassium methoxide.

15. The process of claim 10, wherein the solvent is a $C_5$ to a $C_{12}$ hydrocarbon.

16. The process of claim 15, wherein the hydrocarbon is an aromatic hydrocarbon.

17. The process of claim 16, wherein the aromatic hydrocarbon is selected from the group consisting of xylene, benzene, toluene and chlorobenzene.

18. The process of claim 17, where the hydrocarbon is toluene.

19. The process of claim 10, wherein the racemizing is carried out at a temperature of less than about 20° C.

20. The process of claim 19, wherein the temperature is about 0° C.

21. A process for preparing a pharmaceutically acceptable salt of (S) clopidogrel comprising the steps of:
   a) reacting a first mixture of (R) and (S) clopidogrel with levorotatory camphor sulfonic acid in a mixture of a $C_5$ to a $C_{12}$ hydrocarbon and a suitable co-solvent to precipitate a first (S) clopidogrel camphor sulfonate;
   b) racemizing (R) clopidogrel remaining in the mixture of the hydrocarbon and the co-solvent by reaction with a catalytic amount of a base to obtain a second mixture of (R) and (S) clopidogrel;
   c) precipitating both forms of clopidogrel from the second mixture of (R) and (S) clopidogrel by adding an acid to form a salt;
   d) converting the salt to a free base;
   e) repeating step (a) of the process to obtain a second (S) clopidogrel camphor sulfonate from the free base; and
   f) converting the first and second (S) clopidogrel camphor sulfonate to a pharmaceutically acceptable salt of (S) clopidogrel.

22. The process of claim 21, further comprising a step of removing the co-solvent and excess camphor sulphonic acid in between steps (a) and (b).

23. The process of claim 21, wherein the hydrocarbon is an aromatic hydrocarbon.

24. The process of claim 23, wherein the aromatic hydrocarbon is selected from the group consisting of xylene, benzene, toluene and chlorobenzene.

25. The process of claim 24, wherein the hydrocarbon is toluene.

26. The process of claim 21, wherein the co-solvent is selected from the group consisting of DMF, butanol and acetone.

27. The process of claim 21, wherein the mixture contains from about 3% to about 20% of the co-solvent.

28. The process of claim 27, wherein the mixture contains from about 5% to about 10% of the co-solvent.

29. The process of claim 21, wherein the racemizing is carried out at a temperature of less than about 20° C.

30. The process of claim 29, wherein the temperature is about 0° C.

31. A process for preparing a pharmaceutically acceptable salt of (S) clopidogrel comprising the steps of:
   a) reacting a first mixture of (R) and (S) clopidogrel with levorotatory camphor sulfonic acid in a mixture of a $C_5$ to a $C_{12}$ hydrocarbon and a suitable co-solvent to precipitate a first (S) clopidogrel camphor sulfonate;
   b) racemizing the (R) clopidogrel remaining in the mixture of the hydrocarbon and the co-solvent by reaction with a catalytic amount of a base to obtain a second mixture of (R) and (S) clopidogrel;
   c) reacting the second mixture of (R) and (S) clopidogrel with levorotatory camphor sulfonic acid to precipitate a second (S) clopidogrel camphor sulfonate; and
   d) converting the first and the second (S) clopidogrel camphor sulfonate to a pharmaceutically acceptable salt of (S) clopidogrel.

32. The process of claim 31, wherein the base is selected from the group consisting of sodium methoxide and potassium methoxide.

33. The process of claim 31, wherein the salt is the bisulfate salt.

34. The process of claim 31, further comprising a step of removing co-solvent and excess camphor sulphonic acid between steps (a) and (b).

35. The process of claim 31, further comprising repeating steps (b), (c) and (d) at least once.

36. The process of claim 31, wherein the hydrocarbon is an aromatic hydrocarbon.

37. The process of claim 36, wherein the aromatic hydrocarbon is selected from the group consisting of xylene, benzene, toluene and chlorobenzene.

38. The process of claim 37, wherein the hydrocarbon is toluene.

39. The process of claim 31, wherein the co-solvent is selected from the group consisting of DMF, butanol and acetone.

40. The process of claim 5, 26 or 39, wherein the co-solvent is DMF.

41. The process of claim 31, wherein the mixture contains from about 3% to about 20% (vol/vol) of the co-solvent.

42. The process of claim 41, wherein the mixture contains from about 5% to about 10% of the co-solvent.

43. The process of claim 31, wherein the racemizing is carried out at a temperature of less than about 20° C.

44. The process of claim 43, wherein the temperature is about 0° C.

45. A process for preparing (S) enantiomer of clopidogrel bisulfate comprising the steps of:
   a) reacting a solution of (R) and (S) clopidogrel in toluene with a solution of levorotatory camphor sulfonic acid in DMF, thereby forming a first clopidogrel (S) camphor sulfonate as a precipitate;
   b) removing the DMF and excess camphor sulfonic acid;
   c) racemizing the (R) clopidogrel remaining in the toluene by reaction with a catalytic amount of a base in toluene to form a mixture of clopidogrel (R) and (S);
   d) reacting the mixture of (R) and (S) clopidogrel with levorotatory camphor sulfonic acid in the toluene, thereby forming a second (S) clopidogrel camphor sulfonate as a precipitate; and
   e) converting the first and the second (S) clopidogrel camphor sulfonate to (S) clopidogrel bisulfate.

46. The process of claim 45, wherein the volume of DMF is less than about 20% compared to that of toluene.

47. The process of claim 45, wherein the racemizing is carried out at a temperature of less than about 20° C.

48. The process of claim 47, wherein the temperature is about 0° C.

49. A process for preparing (S) clopidogrel bisulfate comprising the steps of:
   a) reacting a solution of clopidogrel (R) and (S) in toluene with a solution of levorotatory camphor sulfonic acid in DMF, thereby forming a first clopidogrel (S) camphor sulfonate as a precipitate;
   b) removing the DMF and excess camphor sulfonic acid;
   c) racemizing the (R) clopidogrel remaining in the toluene by reaction with a catalytic amount of a base in toluene to form a mixture of (R) and (S) clopidogrel;
   d) adding sulfuric acid to the mixture of (R) and (S) clopidogrel to precipitate clopidogrel (R) and (S) as a bisulfate;
   e) converting the bisulfate to a free base;
   f) repeating step (a) of the process to obtain a second (S) clopidogrel camphor sulfonate from the free base of step (e); and
   g) converting the first and the second (S) clopidogrel camphor sulfonate to (S) clopidogrel bisulfate.

50. The process of claim 49, wherein the volume of DMF is less than about 20% compared to that of toluene.

51. The process of claim 49, wherein the racemizing is carried out at a temperature of less than about 20° C.

52. The process of claim 51, wherein the temperature is about 0° C.

53. A process for preparing (S) clopidogrel bisulfate comprising the steps of:
   a) reacting a solution of (R) and (S) clopidogrel in toluene with a solution of levorotatory camphor sulfonic in DMF, thereby forming (S) clopidogrel camphor sulfonate as a precipitate; and
   b) converting (S) clopidogrel camphor sulfonate to clopidogrel bisulfate.

54. A process for preparing (S) clopidogrel free base or a pharmaceutically acceptable salt thereof comprising the steps of:
   a) reacting a mixture of (R) and (S) clopidogrel free base with levorotatory camphor sulfonic acid in a $C_5$ to a $C_{12}$ hydrocarbon to precipitate (S) clopidogrel camphor sulfonate; and
   b) converting (S) clopidogrel camphor sulfonate to clopidogrel free base or a pharmaceutically acceptable salt thereof.

55. The process of claim 54, wherein the salt is a bisulfate salt.

56. The process of claim 55, wherein the hydrocarbon is an aromatic hydrocarbon.

57. The process of claim 56, wherein the aromatic hydrocarbon is selected from the group consisting of xylene, benzene, toluene and chlorobenzene.

58. The process of claim 57, where the hydrocarbon is toluene.

59. The process of claim 54, comprising a preliminary step of reacting a mixture of clopidogrel (R) and (S) bisulfate with a base.

60. A process for preparing a pharmaceutically acceptable salt of (S) clopidogrel comprising the steps of:
   a) reacting a mixture of (R) and (S) clopidogrel with levorotatory camphor sulfonic acid in a $C_5$ to a $C_{12}$ aromatic hydrocarbon to precipitate (S) clopidogrel camphor sulfonate;
   b) racemizing the (R) clopidogrel remaining in the hydrocarbon by reaction with a catalytic amount of a base in the hydrocarbon to obtain a mixture of (R) and (S) clopidogrel; and
   c) recovering the (S) clopidogrel; and
   d) converting the (S) clopidogrel to a pharmaceutically acceptable salt.

61. The process of claim 60, wherein the hydrocarbon is toluene.

62. The process of claim 60, wherein the base is sodium or potassium t-butoxide.

63. The process of claim 60, wherein the racemizing is carried out at a temperature of less than about 20° C.

64. The process of claim 63, wherein the temperature is about 0° C.

* * * * *